United States Patent [19]

Ortiz

[11] Patent Number: 5,165,794
[45] Date of Patent: Nov. 24, 1992

[54] METHOD FOR THE THERMAL CHARACTERIZATION, VISUALIZATION, AND INTEGRITY EVALUATION OF CONDUCTING MATERIAL SAMPLES OR COMPLEX STRUCTURES

[75] Inventor: Marcos G. Ortiz, Idaho Falls, Id.

[73] Assignee: The United States of America as represented by the United States Department of Energy, Washington, D.C.

[21] Appl. No.: 739,376

[22] Filed: Aug. 2, 1991

[51] Int. Cl.⁵ .............. G01N 25/20; G01N 27/04; G01N 27/18

[52] U.S. Cl. ............................... 374/43; 374/44; 374/137

[58] Field of Search ............ 374/43, 44, 137, 4, 374/5, 57, 53, 166, 183

[56] References Cited

U.S. PATENT DOCUMENTS

| | | | |
|---|---|---|---|
| 2,484,736 | 10/1949 | Razek | 374/44 |
| 3,263,485 | 8/1966 | Mahmoodi | 374/44 |
| 3,721,897 | 3/1973 | Edling | 324/715 |
| 4,176,554 | 12/1979 | Kazmierowicz | 374/137 |
| 4,242,907 | 1/1981 | Kazmierowicz | 374/137 |
| 4,324,138 | 4/1982 | Davis et al. | 374/137 |
| 4,450,509 | 4/1984 | Agarwal | 374/137 |
| 4,730,160 | 3/1988 | Cusack et al. | 374/44 |
| 4,737,917 | 4/1988 | Perron | 374/137 |
| 4,916,715 | 4/1990 | Adiutori | 374/43 |
| 4,933,887 | 6/1990 | Danko et al. | 374/5 |

FOREIGN PATENT DOCUMENTS

| | | | |
|---|---|---|---|
| 0021882 | 2/1977 | Japan | 374/137 |
| 0156593 | 12/1979 | Japan | 374/5 |
| 0117132 | 9/1981 | Japan | 374/137 |
| 0400821 | 10/1973 | U.S.S.R. | 374/137 |
| 0536406 | 11/1976 | U.S.S.R. | 374/43 |
| 0678332 | 8/1979 | U.S.S.R. | 374/166 |

Primary Examiner—William A. Cuchlinski, Jr.
Assistant Examiner—Diego F. F. Gutierrez
Attorney, Agent, or Firm—Helen S. Cordell; John M. Albrecht; William R. Moser

[57] ABSTRACT

A method for modeling a conducting material sample or structure (herein called a system) as at least two regions which comprise an electrical network of resistances, for measuring electric resistance between at least two selected pairs of external leads attached to the surface of the system, wherein at least one external lead is attached to the surface of each of the regions, and, using basic circuit theory, for translating measured resistances into temperatures or thermophysical properties in corresponding regions of the system.

10 Claims, 6 Drawing Sheets

REFERENCE        HIGH

SCALE

TIME = 0

TIME = 10 MINUTES

TIME = 30 MINUTES

METHOD FOR THE THERMAL CHARACTERIZATION, VISUALIZATION, AND INTEGRITY EVALUATION OF CONDUCTING MATERIAL SAMPLES OR COMPLEX STRUCTURES

CONTRACTUAL ORIGIN OF THE INVENTION

The U.S. Government has rights in this invention pursuant to Contract No. DE-AC07-76ID01570 between the U.S. Department of Energy and EG&G IDAHO, INC.

BACKGROUND OF THE INVENTION

This invention relates to non-destructive material evaluation, and in particular, to a method for characterizing, visualizing, and evaluating integrity and thermophysical properties of conducting material samples or complex structures.

A variety of nondestructive evaluation techniques are used for evaluating the integrity of simple and composite materials. They include radiographic (x-ray and neutron), optical, acoustic, ultrasonic, electromagnetic, and thermographic techniques. These various methods are best suited for detecting different types of flaws.

Thermographic methods are based on the principle of thermal imaging of heat patterns. The most common methods of thermal imaging are a chemical method employing liquid crystals and an electronic method employing an infrared camera.

The present invention is useful in the thermal imaging of conducting materials, and is particularly useful in the measurement of thermal conductivity and thermal boundary conditions in composite non-isotropic materials, in material samples of irregular shape, and in materials for high temperature applications.

The present invention has utility a well in characterizing and visualizing the integrity of complex structures (i.e. a machine, a power plant, a chemical plant, etc.) and provides a tool for determining the exact magnitude and location of even small anomalies.

Therefore primary object of this invention is to provide a method for evaluating thermophysical properties of a conducting material sample or structure (herein called a system).

In the accomplishment of the foregoing object, it is another important object of this invention to provide a method for mapping electrical resistance throughout a conducting continuous system.

It is another important object of this invention to provide a graphical representation of a system in terms of its electrical resistance which is useful in visualizing temperature distribution or monitoring the integrity of the system.

It is a further object of this invention to present a method for identifying the dependence of electrical resistance on temperature for a specific system, in both time and steady state.

A yet further object of the present invention is to present a method for system characterization of thermophysical properties which is non-intrusive and non-destructive to the conducting system.

Additional objects, advantages and novel features of the invention will become apparent to those skilled in the art upon examination of the following and by practice of the invention.

SUMMARY OF THE INVENTION

To achieve the foregoing and other objects, this invention comprises a method for modeling a conducting material sample or structure (herein called a system) as an electrical network of resistances, for measuring electric resistance between selected leads attached to the surface of the system, and, using basic circuit theory, for translating measured resistances into temperatures or indications of integrity in corresponding regions of the system.

BRIEF DESCRIPTION OF THE DRAWINGS

The present invention is illustrated in the accompanying drawings where.

DETAILED DESCRIPTION OF THE INVENTION

Figure 1A:
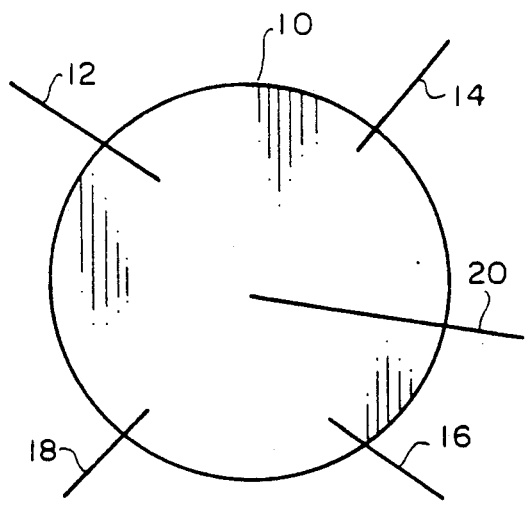
FIGS. 1a, 1b, and 1c are schematic drawings depicting one embodiment and methods of modeling and graphic representation included in the present invention.

FIG. 1a is a schematic drawing which depicts one embodiment of the present invention, showing system 10 and five external leads 12, 14, 16, 18, and 20 which are attached to the surface of system 10 at five locations. In this embodiment, system 10 is a composite, non-isotropic material sample or structure.

Figure 1B:
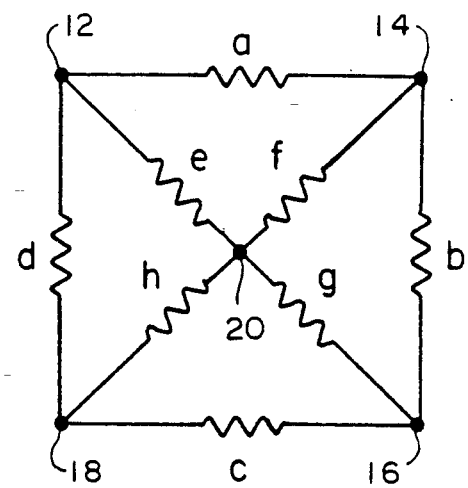

According to the present invention, system 10 and leads 12, 14, 16, 18, and 20 of FIG. 1a are modeled as an electrical network depicted in FIG. 1b, in which electrical resistances a, b, c, d, e, f, g, and h can be measured between external leads 12, 14, 16, 18 and 20 as depicted. Those skilled in the art will recognize that in other embodiments more or less complex configurations with a variable number of regions may be selected based on the system's geometry and the purpose of the study.

Figure 1C:
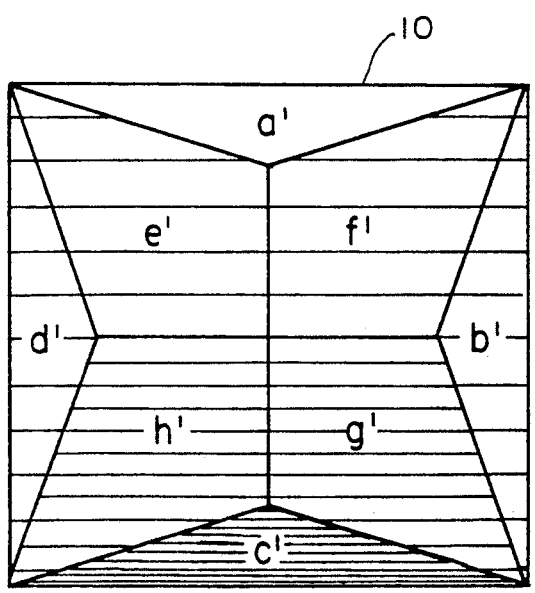
Figure 1C:
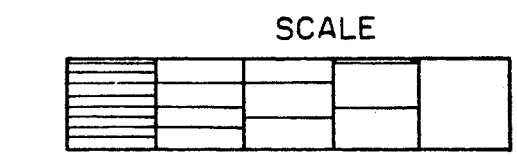

FIG. 1c is a schematic drawing which depicts system 10 divided into regions a', b', c', d', e', f', g', and h'. According to the method of the present invention, each of these regions is associated with a corresponding hypothetical resistance which cannot be measured independently. The present invention analogizes that the system is an electrical network such as shown in FIG. 1b, that localized changes of temperature or structure integrity will produce changes in measurable resistances a, b, c, d, e, f, g, and h, and that given those changes functional relationships ca be established with the respective hypothetical resistances.

Proceeding on this analogy, the present invention uses basic circuit theory known to those skilled in the prior art to describe the functional relationships of the network shown in FIG. 1b in eight non-linear algebraic equations:

$$F_1(a,b,c,d,e,f,g,h) = R_{12,20}$$
$$F_2(a,b,c,d,e,f,g,h) = R_{14,20}$$
$$F_3(a,b,c,d,e,f,g,h) = R_{16,20}$$
$$F_4(a,b,c,d,e,f,g,h) = R_{18,20} \quad (1)$$
$$F_5(a,b,c,d,e,f,g,h) = R_{12,14}$$
$$F_6(a,b,c,d,e,f,g,h) = R_{14,16}$$
$$F_7(a,b,c,d,e,f,g,h) = R_{16,18}$$
$$F_8(a,b,c,d,e,f,g,h) = R_{18,12}$$

The right hand side of each of these equations represents one of eight experimental measurements between selected leads attached to system 10 in FIG. 1a. Subscripts of R refer to leads selected for measurement, comprising leads 12, 14, 16, 18 and 20 shown in FIG. 1a. Those skilled in the art will recognize that a similar analysis will result if a current is imposed by an external source between any two leads, and the voltage of all leads is measured with respect to a common ground.

Solving the above network equations yields multiple solutions for values of resistance within each region of the sample. The real and positive solution is assigned to electrical resistance in each region of the system. Resistances throughout the system can then be visualized in a two dimensional computerized image by scaling the resistances to a chosen norm and depicting variation from the norm by a color or shade of grey, as depicted in FIG. 1c.

The present invention is also useful in defining the dependence of resistance on temperature for different regions of the system.

First, resistances within system 10 are calibrated with respect to a given temperature by performing measurements between selected leads as shown in Eqs. 1 while system 10 is maintained uniformly at a first temperature in a constant temperature environment. Subsequently measurements are performed between the same selected leads while system 10 is maintained uniformly at other temperatures within a range of interest. Thus, a direct correspondence is established between the evaluated resistance in each region of the system and each of the temperatures at which the system was maintained.

If the system is then exposed to uneven temperature, and resistance is measured between the same selected leads, the resultant measurements can be correlated to temperature and then used to create a temperature map, showing relative temperatures in each region of the system.

If changes in temperature are both uneven and slower than the rate at which measurements are taken, and thermophysical properties are known, measurements of electrical resistance can be used to determine heat fluxes through the system. Or, if applied heat fluxes are known, measurements of electrical resistance can be used to determine thermophysical properties. The method is thus particularly suited to evaluation of non-isotropic materials or composites, for it determines the direction in which heat flux is going, and an experiment can be designed to accurately evaluate a known anistropy of a material.

Figure 2:
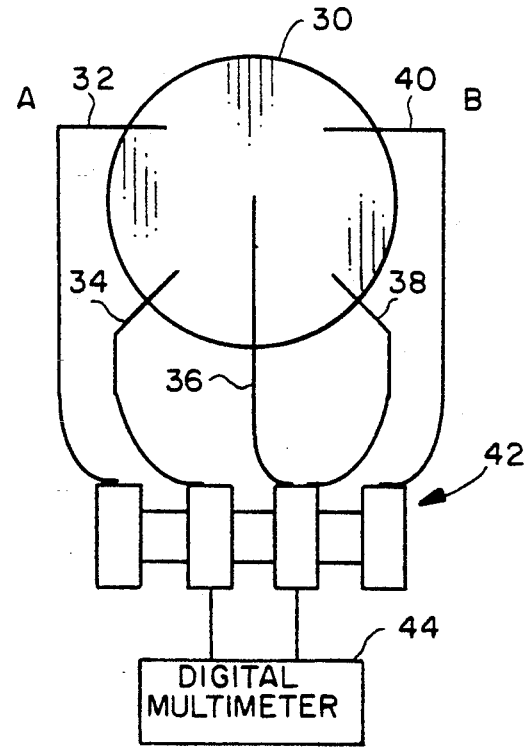
FIG. 2 is a schematic drawing showing external leads attached to a system and measurement of electrical resistance between those external leads.

In an embodiment of the present invention shown in FIG. 2, graphite powder is added to material sample 30— a 0.682 kg disk of clay, approximately 12 cm in diameter and 3 cm thick. Sample 30 is sealed in a thin plastic cover to prevent drying and firmly attached to a wooden board (not shown). Five copper leads 32, 34, 36, 38 and 40 are buried in sample 30 at specific locations. A battery of switches 42 fixed to the same board allows for independent measurement of electrical resistance between selected pairs of leads without need to reconnect or rewire the circuit. Measurements of electrical resistances are performed using a digital multimeter 44. It will be apparent to those skilled in the art that a variety of instruments may be substituted for multimeter 44, including a computer and data acquisition system which perform resistance measurements automatically.

Figure 3:
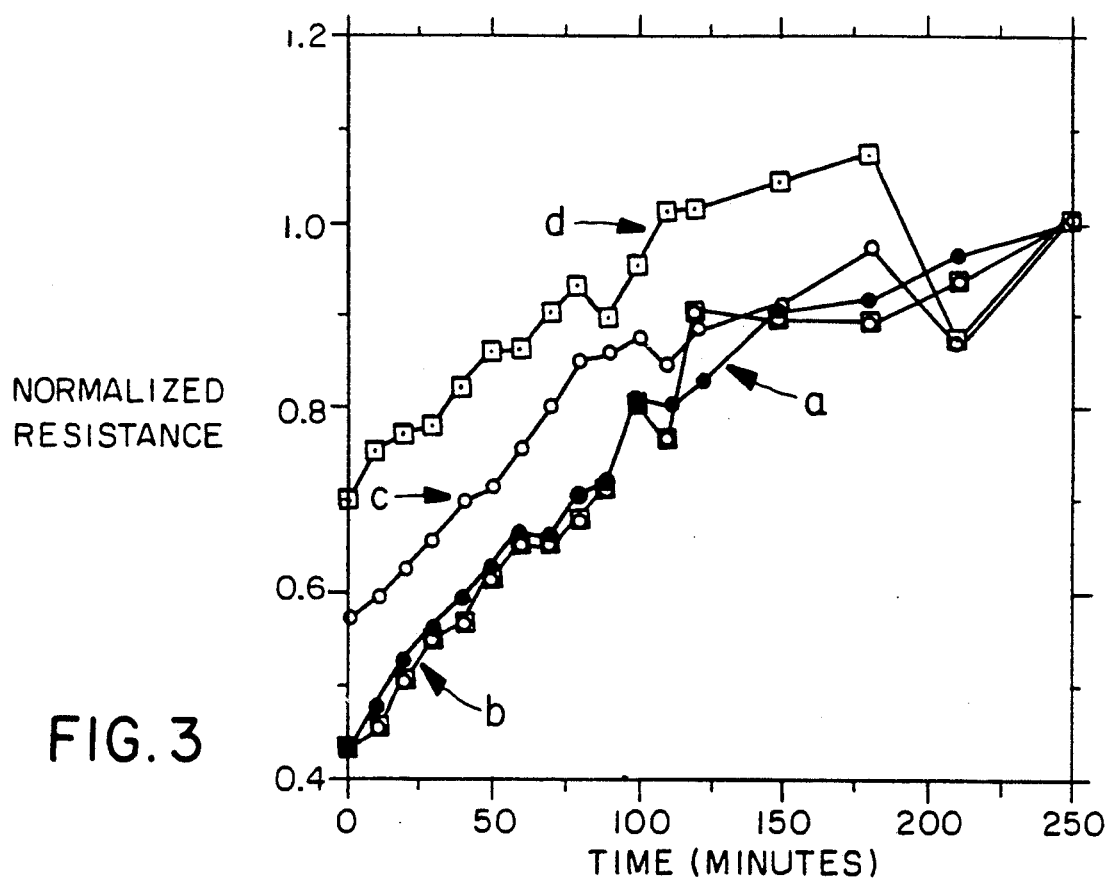
FIGS. 3 and 4 are graphs depicting measurements derived from an embodiment of the present invention, showing calculated resistance measurements with respect to time for a material sample which was first heated and then left to cool.
Figure 4:
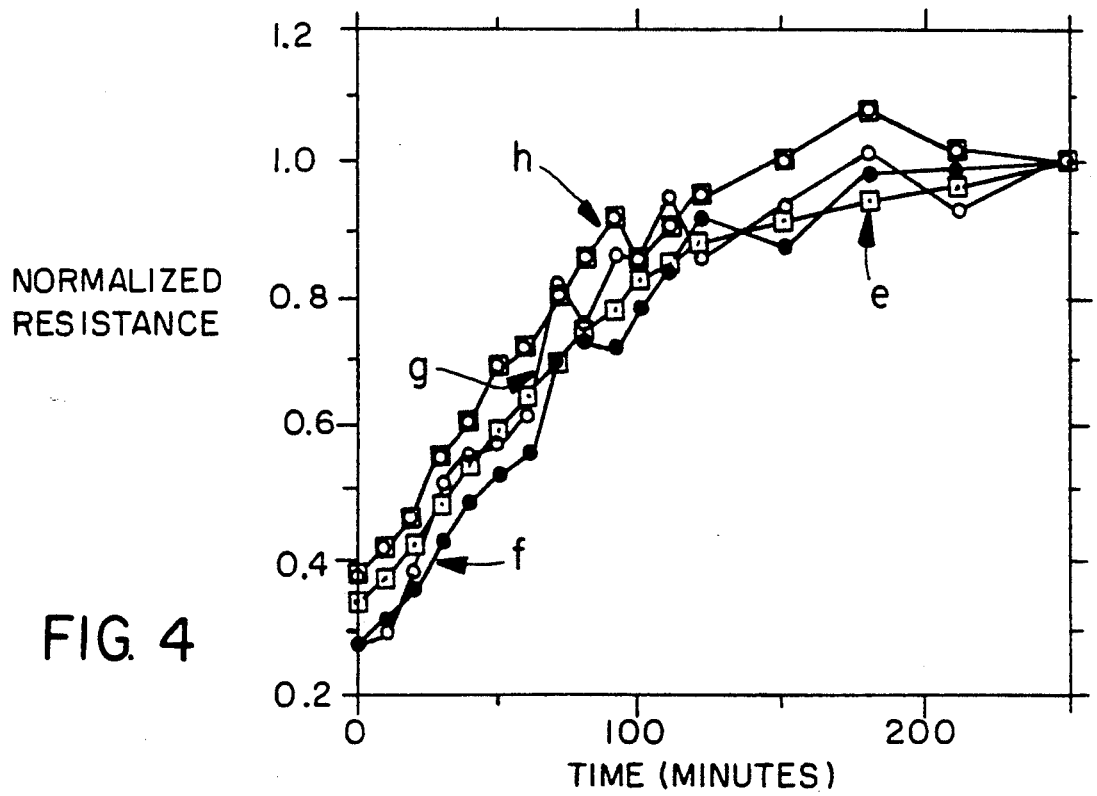

FIGS. 3 and 4 are graphs showing resistance measurements made on sample 30 after it has been in an oven at 332 K for several hours and is left to cool at room temperature (300 K) while the measurements are being performed. FIG. 3 shows resistance measurements between external leads corresponding to resistances a, b, c, and d in FIG. 1b. FIG. 4 shows measurements between external leads and the center lead, corresponding to resistances e, f, g, and h of FIG. 1b. Measurements are normalized with respect to the final value (room temperature) to gather them together in one trend. Comparison of the two figures shows that the inside of the sample (FIG. 4) cools more uniformly than the outside (FIG. 3). Large variations may be attributed to changes in the contact area between copper leads buried in the clay and the clay itself, resulting from different coefficients of expansion between clay and graphite in the sample, and by voids of varying dimensions inside the sample.

Figure 5:
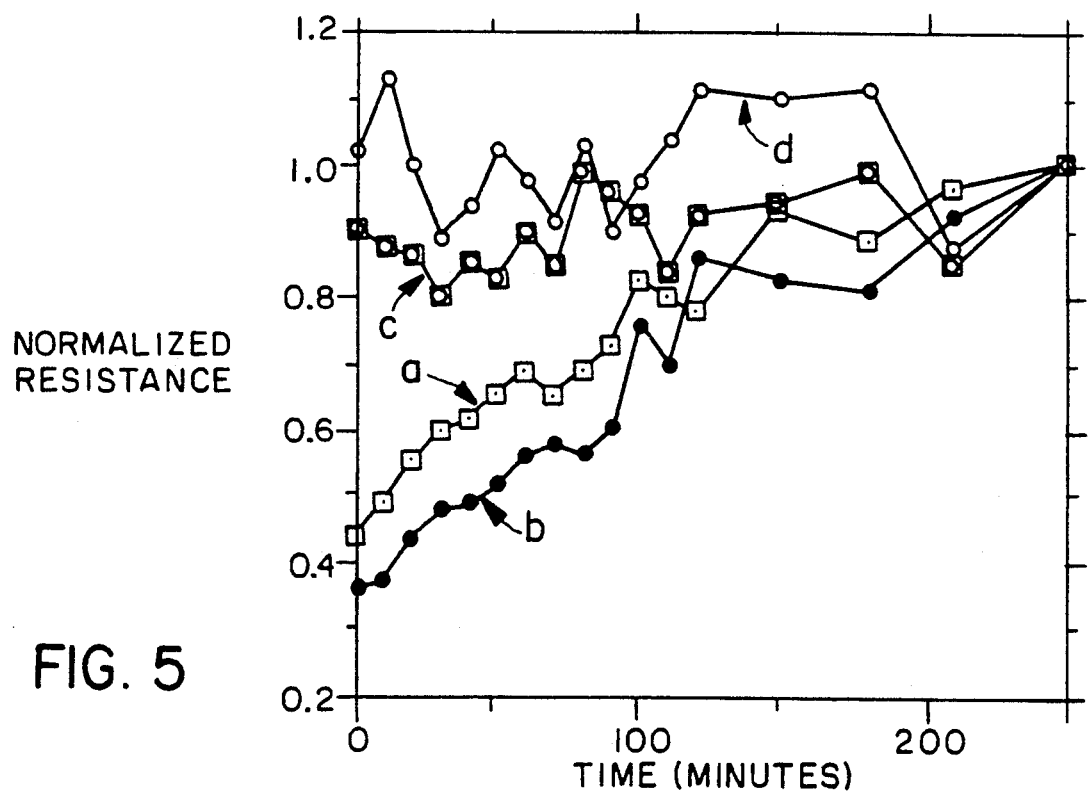
FIGS. 5 and 6 are graphs showing variations of calculated network resistances which correspond to data depicted in FIGS. 3 and 4.
Figure 6:
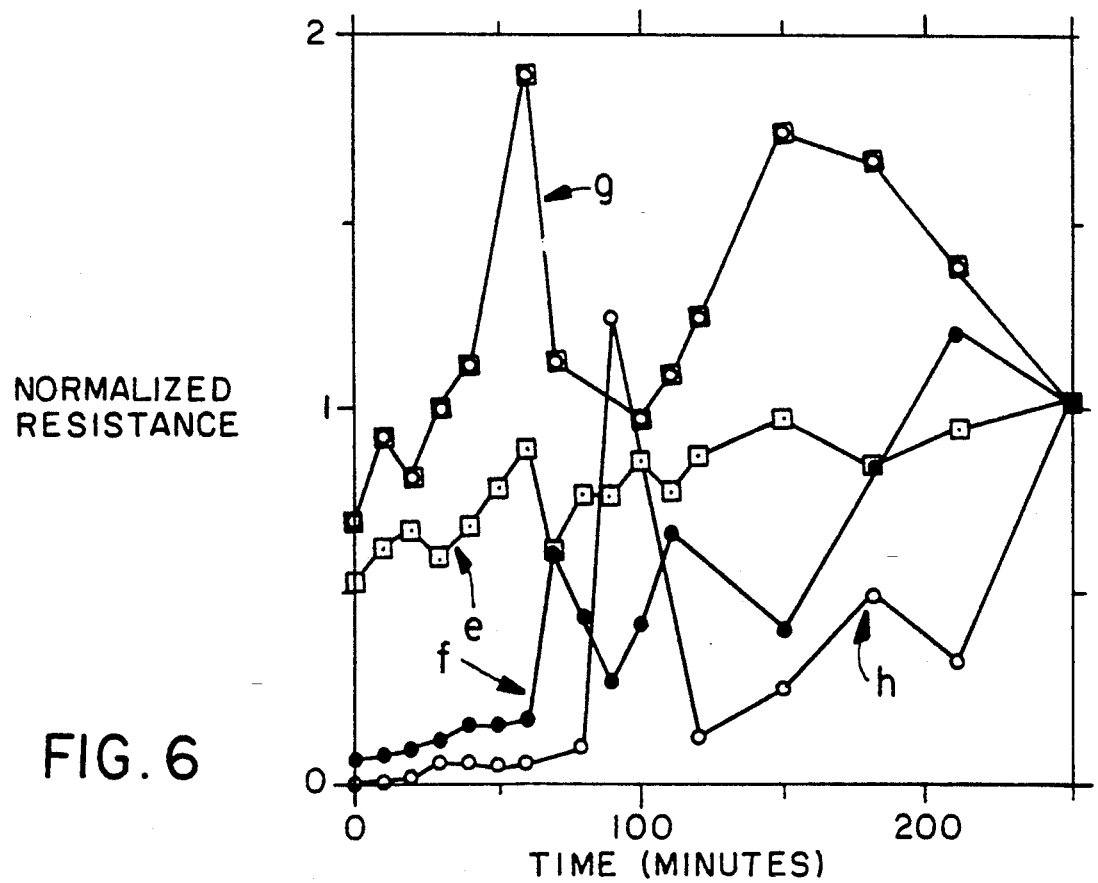

FIGS. 5 and 6 show the variation of the calculated network resistances (again normalized with respect to their values at room temperature) which correspond to data in FIGS. 3 and 4. Despite the increased scatter of points, a trend similar to the one in FIGS. 3 and 4 can be identified. The results also indicate that a region of sample 30 (corresponding to the lower left corner of FIG. 1c, resistances c, d, g, and h) shows more erratic behavior than the other region (upper right corner, resistances a, b, e, and f). The same region of erratic behavior also shows the largest values of electrical resistance.

Figure 7:
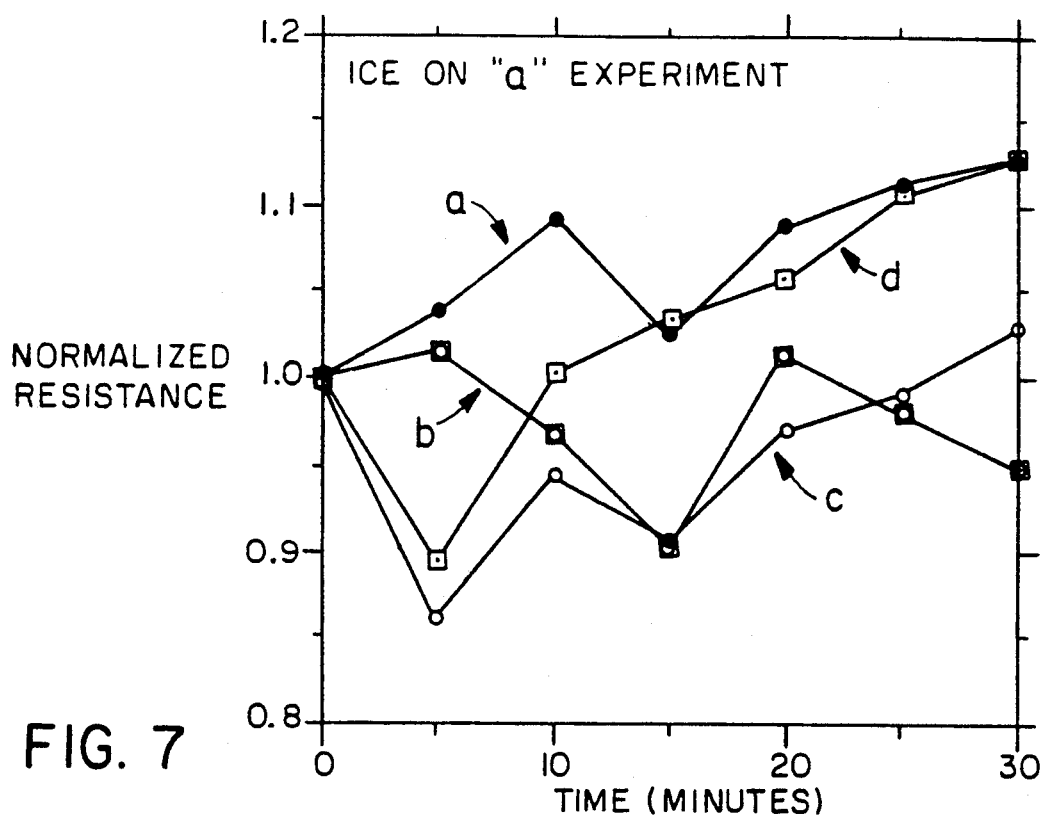
FIGS. 7 and 8 are graphs depicting measurements showing calculated resistance measurements with respect to time for a material sample when ice is placed against the sample.
Figure 8:
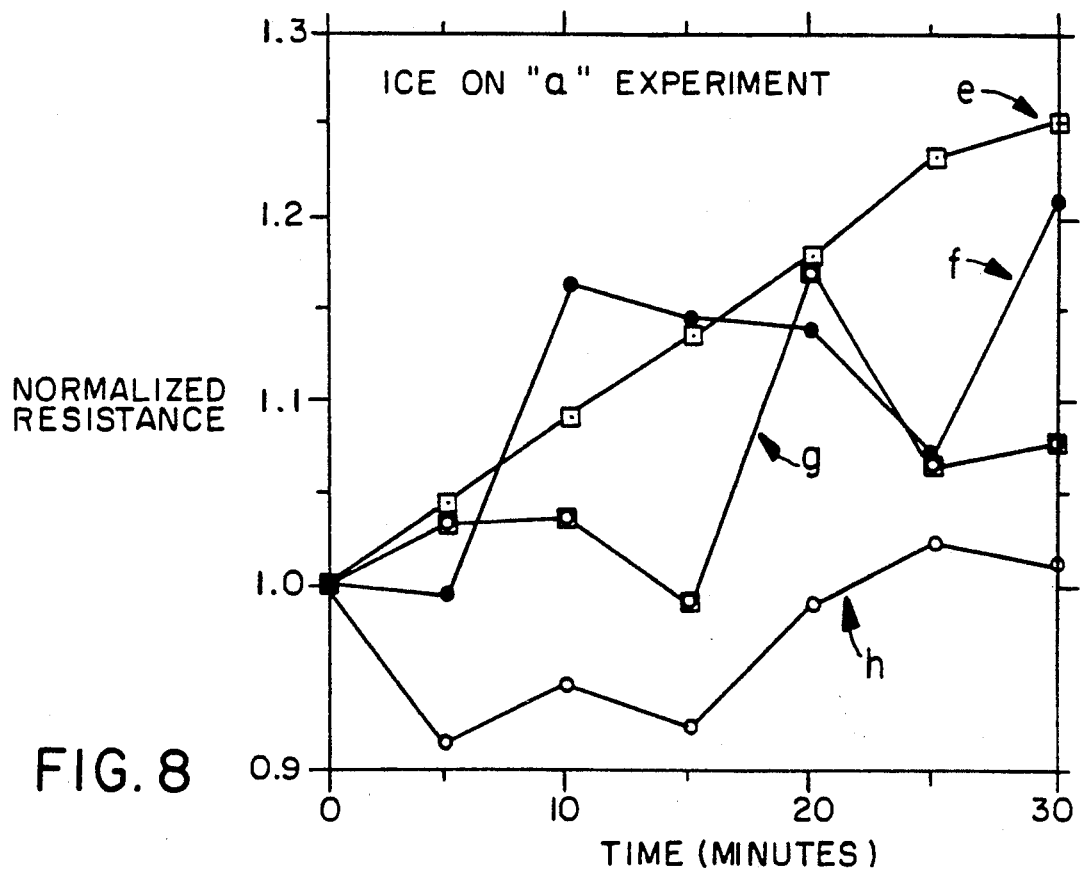

After sample 30 attains equilibrium at room temperature, a bag of ice is placed and held in contact with sample 30 in the region between leads 32 and 40 shown in FIG. 2. Resistance is measured every five minutes and the resulting normalized resistance history is shown in FIGS. 7 and 8. Values of resistance close to the ice tend to change according to established trends of FIGS. 3 and 4, whereas resistances distant from the ice do not.

Figure 9A:
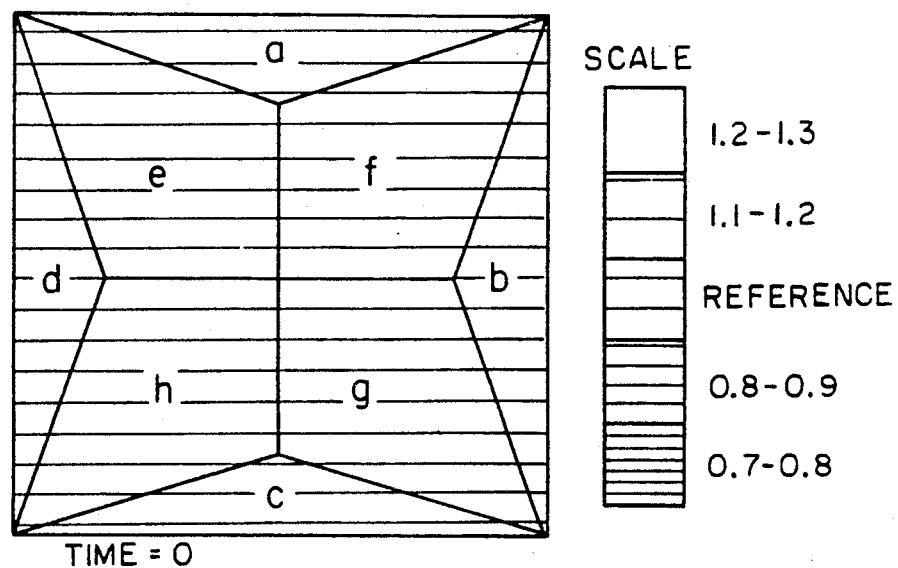
FIGS. 9a, 9b and 9c are two dimensional visualizations of direct measurements of resistance at different instants of time when ice is placed against one side of the sample, causing non-uniform temperature distribution.
Figure 9B:
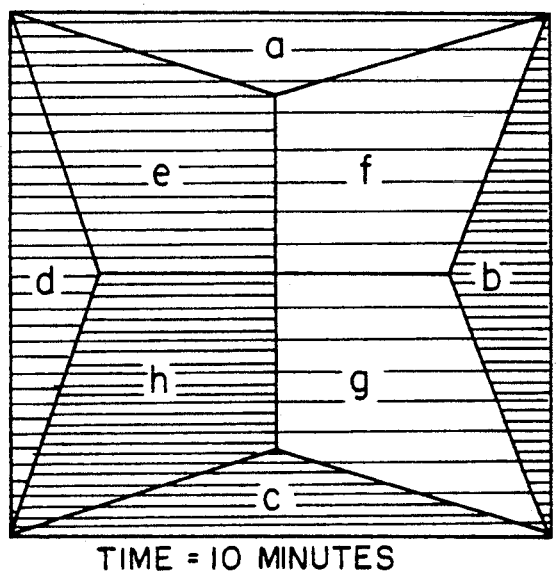
Figure 9C:
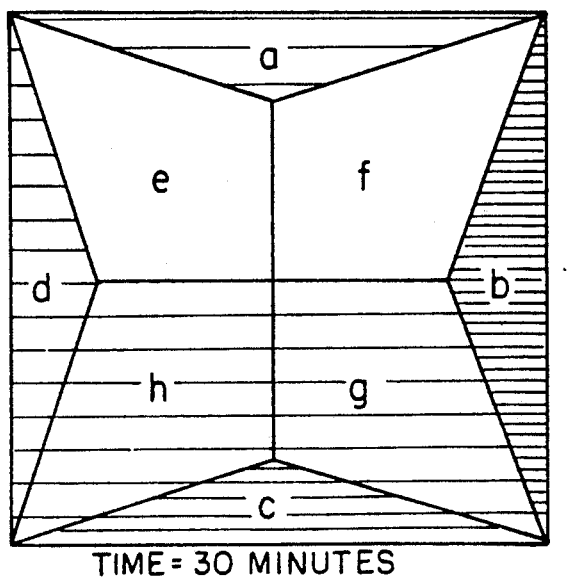

FIGS. 9a, 9b, and 9c are two dimensional visualizations of direct measurements of resistance at different instants of time when (as in FIG. 7 and 8) a piece of ice is placed against a region of the sample. Direct measurements are used because the erratic behavior of the clay makes it very difficult for the algorithm to converge to a solution of Eqs. (1). In FIG. 9a, reference is established at time =0, before the ice is placed against the sample. FIG. 9b depicts measurements at time=10 minutes and FIG. 9c shows measurements at time=30 minutes.

The non-homogeneity of the sample becomes evident in this type of representation. FIGS. 9a, 9b, and 9c demonstrate that direct measurements are an alternate and rapid way of arriving at an approximate two dimensional characterization of the system.

The present invention is useful as well in evaluating boundary conditions. Since the method of the present invention does not require that the entire sample be at the same temperature, it is possible to locally heat a system in any identified region to a very high temperature, even melting. An abrupt change in electrical resistance accompanying melting will serve as an indicator of melting point. For example, for a high temperature application material, it would be possible to melt only the center portion of the sample (for example with a laser beam), and then track the temperature history of that region before, during and after melting, thereby determining both melting point and thermal conductivity of the solid surrounding the molten pool at the high temperature.

Figure 10A:
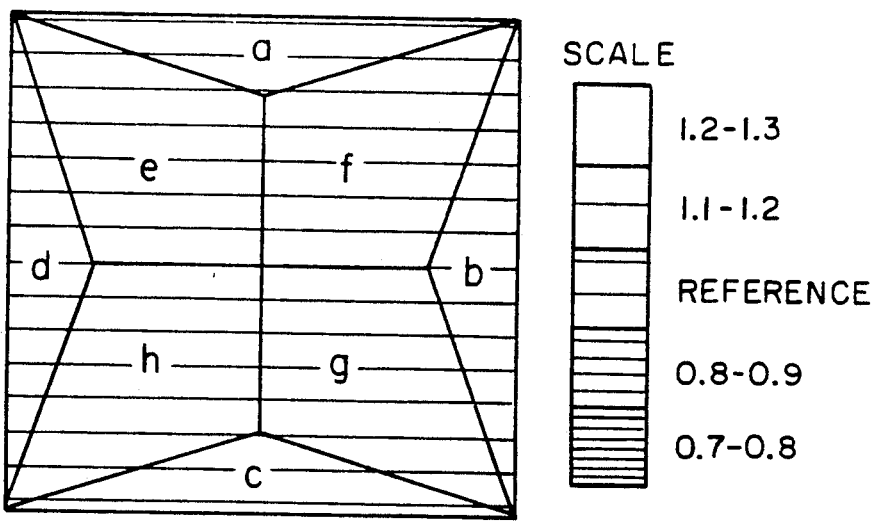
FIGS. 10a, 10b, and 10c are two dimensional visualizations of direct measurements of resistance after damage to a network.
Figure 10B:
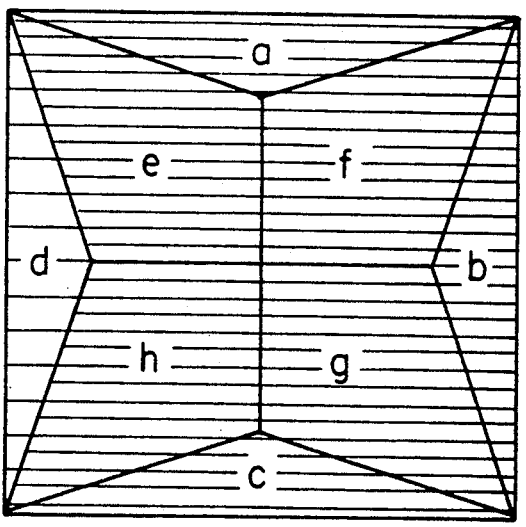
Figure 10C:
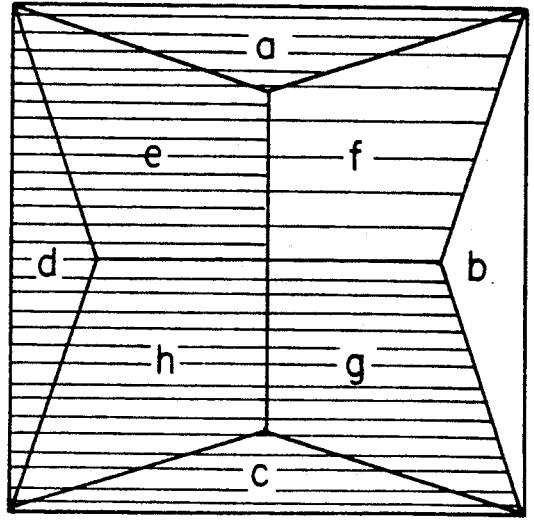

A primary application of the present invention is to the monitoring and evaluation of the integrity of a system. The utility of two dimensional characterization is also evident in FIGS. 10a, 10b, and 10c, depicting direct measurements after damage to the network of FIG. 1b. FIG. 10a establishes a reference. FIG. 10b depicts a 30% break (increase) in resistance d of FIG. 1b, and FIG. 1c depicts a 60% break in resistance b of FIG. 1b. The damage is not only located, but the magnitude of difference between the two breaks results in a different shade distribution enabling evaluation of damage to the integrity of the system.

In summary, the present invention is a method for evaluating thermophysical properties of conducting material samples and structures. It provides a method for mapping electrical resistance throughout a conducting continuous system, for identifying the dependence of resistance on temperature, and for determining patterns of heating and cooling under uneven temperature or heat flux boundary conditions. As a method for system characterization, it is suitable for monitoring, evaluating, and visualizing the integrity of small material samples or systems as large as an operating plant, enabling identification of even small anomalies without intrusion or destruction.

The embodiments of this invention in which an exclusive property or privilege is claimed are defined as follows:

1. A method for determining thermophysical properties of a conducting system, including:
   characterizing said system as at least two regions which comprise an electrical network of resistances, in which each resistance in said network corresponds to a region of said system,
   attaching at least one external lead to the surface of each of said regions and measuring electrical resistances between at least two selected pairs of said external leads, and
   using basic circuit theory, translating said measured resistances into thermophysical properties in said regions of said system.

2. The method of claim 1 wherein said measuring of electrical resistances between selected pairs of external leads is performed sequentially.

3. The method of claim 1 wherein said measuring of electrical resistances between selected pairs of external leads is performed simultaneously.

4. The method of claim 1 wherein said characterizing includes characterizing said system as a network in which an electrical path is drawn between each lead pair and a central location, and said measuring includes measuring said electrical resistances by imposing a current between said leads and measuring the voltage between said leads with respect to a common ground.

5. The method of claim 4 wherein said translating includes solving network equations to determine values of resistance within each of said regions of said system.

6. The method of claim 5 including defining the dependence of resistance on temperature within each of said regions of said system, by measuring electrical resistance within each of said regions while said system is uniformly maintained at a first temperature, in a constant temperature environment, subsequently measuring said electrical resistances while said system is uniformly maintained at second and subsequent temperatures, and establishing a calibration between said measured electrical resistances and said temperatures.

7. The method of claim 6 including determining the temperature of one or more regions of said system when said system is exposed to non-uniform temperatures by measuring electrical resistance within each of said regions and correlating said measured resistances with said calibration.

8. The method of claim 7 wherein said non-uniform temperatures to which said system is exposed create heat flux boundary conditions.

9. The method of claim 8 wherein said non-uniform temperatures create melting in at least one region of said system.

10. The method of claim 7 including graphically representing said temperatures as a function of time.

* * * * *